United States Patent
Burdett et al.

(10) Patent No.: US 7,696,398 B2
(45) Date of Patent: Apr. 13, 2010

(54) STABILIZATION OF OLEFIN METATHESIS PRODUCT MIXTURES

(75) Inventors: Kenneth A. Burdett, Midland, MI (US); Rob R. Maughon, Midland, MI (US); Patrick H. Au-Yeung, Midland, MI (US)

(73) Assignee: Dow GlobalTTechnologies, Inc., Midland, MI (US)

( * ) Notice: Subject to any disclaimer, the term of this patent is extended or adjusted under 35 U.S.C. 154(b) by 1393 days.

(21) Appl. No.: 10/528,472

(22) PCT Filed: Sep. 26, 2003

(86) PCT No.: PCT/US03/30632

§ 371 (c)(1),
(2), (4) Date: Mar. 21, 2005

(87) PCT Pub. No.: WO2004/037754

PCT Pub. Date: May 6, 2004

(65) Prior Publication Data

US 2006/0167326 A1    Jul. 27, 2006

Related U.S. Application Data

(60) Provisional application No. 60/421,355, filed on Oct. 24, 2002.

(51) Int. Cl.
*C07C 6/00* (2006.01)
*C07C 7/00* (2006.01)
(52) U.S. Cl. ............... 585/646; 585/643; 585/647; 585/800; 585/809
(58) Field of Classification Search ............ 585/820, 585/800, 643, 646, 647, 809
See application file for complete search history.

(56) References Cited

U.S. PATENT DOCUMENTS

| | | | |
|---|---|---|---|
| 4,545,941 | A | 10/1985 | Rosenburg |
| 4,560,792 | A | 12/1985 | Banasiak |
| 4,772,758 | A | 9/1988 | Kaufhold |
| 4,943,397 | A | 7/1990 | Johnson |
| 5,143,885 | A | 9/1992 | Warwel et al. |
| 5,218,131 | A | 6/1993 | Warwel et al. |
| 5,312,940 | A | 5/1994 | Grubbs et al. |
| 5,342,985 | A | 8/1994 | Herrmann et al. |
| 5,352,812 | A | 10/1994 | Feldman et al. |
| 5,539,060 | A | 7/1996 | Tsunogae et al. |
| 5,932,664 | A | 8/1999 | Chen et al. |
| 6,060,572 | A | 5/2000 | Gillis et al. |
| 6,156,692 | A | 12/2000 | Nubel et al. |
| 6,197,894 | B1 | 3/2001 | Sunaga et al. |
| 6,635,768 | B1 | 10/2003 | Herrmann et al. |
| 7,176,336 | B2 | 2/2007 | Maughon et al. |
| 2005/0154221 | A1 | 7/2005 | Lysenko et al. |
| 2008/0103346 | A1 | 5/2008 | Burdett et al. |
| 2008/0228017 | A1 | 9/2008 | Burdett et al. |

FOREIGN PATENT DOCUMENTS

| | | |
|---|---|---|
| DE | 4107056 A1 | 8/1990 |
| DE | A1-281594 | 8/1990 |
| DE | 100 41 345 | 3/2002 |
| EP | 0 084 437 A1 | 7/1983 |
| EP | 0 099 572 B2 | 2/1984 |
| EP | 0 328 230 | 8/1989 |
| JP | 56 077243 | 6/1981 |
| JP | 03 066725 A | 3/1991 |
| JP | 03066725 | 3/1991 |
| WO | WO 91/14665 | 10/1991 |
| WO | WO 93/20111 | 10/1993 |
| WO | WO 96/04289 | 2/1996 |
| WO | WO 97/06185 | 2/1997 |
| WO | WO 99/00397 | 1/1999 |
| WO | WO 99/22866 | 5/1999 |
| WO | WO 00/15339 | 3/2000 |
| WO | WO 00/58322 | 10/2000 |
| WO | WO 00/71554 | 11/2000 |
| WO | WO 02/076920 | 10/2002 |

(Continued)

OTHER PUBLICATIONS

Ahn, Yu Mi et al., "A Convenient Method for the Efficient Removal of Ruthenium Byproducts Generated During Olefin Metathesis Reactions", Organic Letters, vol. 3, pp. 1411-1413 (2001).

(Continued)

*Primary Examiner*—In Suk Bullock

(57) ABSTRACT

A process of stabilizing an olefin metathesis product mixture, preferably, against double bond isomerization and thermal and chemical degradation. The process involves (a) contacting an olefin metathesis product mixture comprising one or more olefins produced in a metathesis process, a metathesis catalyst comprising a catalytic metal and one or more ligands, optionally, one or more metathesis catalyst degradation products, and optionally, one or more metals derived from sources other than the catalyst or catalyst degradation product(s), with an adsorbent, more preferably carbon; or alternatively, (b) subjecting the olefin metathesis product mixture to a two-step distillation, preferably, including short path wiped-film evaporation. A stabilized olefin metathesis product mixture to a two-step distillation, preferably, including short path wiped-film evaporation. A stabilized olefin metathesis product mixture is disclosed containing one or more olefins obtained in a metathesis process and having a total concentration of metal(s) of less than about 30 parts per million by weight.

14 Claims, No Drawings

FOREIGN PATENT DOCUMENTS

| WO | WO 03/093215      | 11/2003 |
|----|-------------------|---------|
| WO | WO 2004/030020    | 9/2004  |
| WO | WO 2006/132902    | 12/2006 |
| WO | WO 2008/027267 A2 | 3/2008  |
| WO | WO 2008/027268 A2 | 3/2008  |
| WO | WO 2008/027269 A2 | 3/2008  |
| WO | WO 2008/027283 A2 | 3/2008  |

OTHER PUBLICATIONS

Biermann, Ursula et al., "New Synthesis with Oils and Fats as Renewable Raw Materials for the Chemical Industry", Angewandte Chemie Int. Ed., vol. 39, pp. 2207-2224 (2000).

Buchowicz, W. et al., "Catalytic Activity and Selectivity of Ru(=CHPh)Cl$_2$(PCy$_3$)$_2$ in the Metathesis of Linear Alkenes", Journal of Molecular Catalysis A: Chemical, vol. 148, pp. 97-103 (1999).

Derwent Abstract, AN 1991-015326 (DD 281594).

Dowden, James et al., "Olefin Metathesis in Non-Degassed Solvent Using a Recyclable, Polymer Supported Alkylideneruthenium", Chemical Communications, pp. 37-38 (2001).

Gessler, Simon et al., "Synthesis and Metathesis Reactions of a Phosphine-Free Dihydroimidazole carbine Ruthenium Complex", Tetrahedron Letters, vol. 41, pp. 9973-9976 (2000).

Kingsbury, Jason et al., "A Recyclable Ru-Based Metathesis Catalyst", Journal of the American Chemical Society, vol. 121, pp. 791-799 (1999).

Mandelli, Dalmo et al., "Ethenolysis of Esters of Vegetable Oils: Effect of B$_2$O$_3$ Addition to Re$_2$O$_7$/SiO$_2$.Al$_2$O$_3$-SnBu$_4$ and CH$_3$ReO$_3$/SiO$_2$.Al$_2$O$_3$ Metathesis Catalysts", Journal of the American Oil Chemical Society, vol. 73, pp. 229-232 (1996).

Maynard, Heather et al., "Purification Technique for the Removal of Ruthenium from Olefin Metathesis Reaction Products", Tetrahedron Letters, vol. 40, pp. 4137-4140 (1999).

Nubel, P.O. et al., "A Convenient Catalyst System Employing RuCl$_3$ or RuBr$_3$ for Metathesis of Acyclic Olefins", Journal of Molecular Catalysis A: Chemical, vol. 145, pp. 323-327 (1999).

Paquette, Leo et al., "A Convenient Method for Removing All Highly-Colored Byproducts Generated During Olefin Metathesis Reactions", Organic Letters, vol. 2, pp. 1259-1261 (2000).

Refvik, M.D. et al., "Ruthenium-Catalyzed Metathesis of Vegetable Oils", Journal of the American Oil Chemical Society, vol. 76, pp. 93-98 (1999).

Warwel, Siegfried et al., "Polymers and Surfactants on the Basis of Renewable Resources", Chemosphere, vol. 43, pp. 39-48 (2001).

Yao, Qingwei, "A Soluble Polymer-Bound Ruthenium Carbene Complex: A Robust and Reusable Catalyst for Ring-Closing Olefin Metathesis", Angewandte Chemie Intl. Ed., vol. 39, pp. 3896-3898 (2000); (German version: Yao, Qingwei, "Ein löslicher, polymergebundener rutheniumcarbenkomplex: ein robuster und wiederverwendbarer Katalysator für Ringschluss-Olefinmetathesen", Angewandte Chemie, vol. 112, pp. 4060-4063 (2000)).

"An Improved Process for the Synthesis of Unsaturated Alcohols", filed in the United States of America on Oct. 9, 2003, U.S. Appl. No. 60/509,908; Applicant; Bob R. Maughon et al.

"An Improved Process for the Synthesis of Unsaturated Alcohols", filed in the United States of America on Sep. 14, 2004, U.S. Appl. No. 10/940,403; Applicant; Bob R. Maughon et al.

"Integrated Chemical Processes for Industrial Utilization of Seed Oils", filed in the United States of America on Apr. 17, 2003, U.S. Appl. No. 10/508,805; Applicant; Zenon Lysenko, et al.

"Metathesis of Unsaturated Fatty Acid Esters or Unsaturated Fatty Acids with Lower Olefins", filed in the United States of America on Feb. 27, 2002, U.S. Appl. No. 10/469,321; Applicant; Thomas H. Newman, et al.

Burdett, Kenneth A., "Renewable Monomer Feedstocks via Olefin Metathesis: Fundamental Mechanistic Studies of Methyl Oleate Ethenolysis with the First-Generation Grubbs Catalyst", Organometallics, vol. 23, pp. 2027-2047, 2004.

Copending U.S. Appl. No. 11/915,794, filed Nov. 28, 2007, in the names of Kenneth A Burdett, Morteza Mokhtarzadeh and Francis J. Timmers, for "Metathesis Process for Preparing an Alpha, Omega-Functionalized Olefin,"; equivalent to WO 2006/132902.

STABILIZATION OF OLEFIN METATHESIS PRODUCT MIXTURES

CROSS REFERENCE TO RELATED APPLICATIONS

This application claims the benefit of U.S. provisional patent application Ser. No. 60/421355, filed on Oct. 24, 2002.

BACKGROUND OF THE INVENTION

In a first aspect, this invention pertains to a process of stabilizing an olefin metathesis product mixture, preferably, against double bond isomerization and thermal and chemical decomposition. In a second aspect, this invention pertains to a stabilized olefin metathesis product composition. In a third aspect, this invention pertains to methods for removing metals from an olefin metathesis product mixture.

Olefin metathesis processes commonly involve the conversion of two reactant olefins in the presence of a metathesis catalyst into one or more product olefins that are different from the reactant olefins. If the two reactant olefins are chemically different compounds, then the process is referred to as "hetero-metathesis." If the two reactant olefins are chemically identical compounds, then the process is referred to as "homo-metathesis." In a different, but yet related manner, olefin metathesis processes also include ring-opening metathesis polymerization reactions wherein an unsaturated cyclic compound is ring-opened and polymerized to form an unsaturated polymer. In yet another type of olefin metathesis process, a reactant alkene and reactant alkyne can be cross-metathesized to form a conjugated 1,3-diene. The prior art discloses homogeneous and heterogeneous metathesis catalysts that comprise at least one catalytically active metal, such as ruthenium, molybdenum, tungsten, or rhenium, and one or more ligands complexed to the metal(s).

Metathesis processes find utility in converting olefin feedstocks of low commercial value into unsaturated products of higher commercial value. By way of example, a long chain internal olefin, such as methyl oleate, obtainable from seed oils, can be metathesized with a lower olefin, such as a $C_{2-8}$ olefin, preferably ethylene, in the presence of a metathesis catalyst to yield two product olefins of intermediate chain length, for example, 1-decene and methyl 9-decenoate. Intermediate length α-olefins, such as 1-decene, are useful in the preparation of poly(olefin) polymers. Alpha, omega (α,ω) ester-functionalized olefins, such as methyl 9-decenoate, can be converted into polyester polyepoxides, polyester polyalcohols or polyester polyamines, all of which find utility in the preparation of thermoset polymers, such as epoxy resins and polyurethanes.

Olefin metathesis product mixtures typically comprise one or more product olefins, a metal-ligand metathesis complex catalyst, optionally, metathesis catalyst degradation products, optionally, metathesis reaction by-products, and optionally, unconverted reactant olefins. As noted hereinabove, the metathesis catalyst comprises at least one catalytically active metal complexed to a catalytically active combination of one or more organic and/or inorganic ligands. Metathesis catalyst degradation products include ligand degradation products obtained when the ligand is oxidized by residual oxygen or otherwise reacted in a disadvantageous manner during the metathesis process. Metathesis degradation products may also include metal-ligand degradation product complexes. Finally, metathesis catalyst degradation products may also include catalytically inactive complexes produced when the catalytic metal binds to any available ligand to form a catalytically inactive complex. Olefin metathesis product mixtures may also contain extraneous metals added as catalyst promoters to the metathesis process or leached into the metathesis reaction from a catalyst support, a heterogeneous catalyst, or reactors and conduit pipes.

Homogeneous catalysts, while particularly active and selective, present a problem in that for economical purposes, the catalyst (including catalytic metal) should be recovered from the olefin metathesis product mixture. More importantly, it has been recognized that metathesis catalysts and catalyst degradation products destabilize olefin metathesis product mixtures against isomerization (double bond migration), which produces undesirable isomeric by-products different from the target products or the reactant olefins, as the case may be. Such undesirables reduce product selectivity and waste raw materials. The destabilization is generally more pronounced at elevated temperatures. Since product separation by distillation typically requires a higher temperature than that of metathesis, destabilization is more likely during the separation process. As a further disadvantage, metathesis catalysts and catalyst degradation products can destabilize olefin metathesis product mixtures against thermal and chemical decomposition. Over time, during storage or at elevated temperatures, undesirable thermal or chemical reactions may occur, further resulting in unrecoverable raw material losses and low product olefin yields. Such adverse effects are generally attributed to the presence of the catalytic metal(s) in the metathesis catalyst and catalyst degradation products. Similar adverse effects can also be induced by promoter metals that are deliberately added to the metathesis reaction to enhance catalyst performance or by extraneous metals that leach into the metathesis reaction mixture from catalyst supports, heterogeneous catalysts, metallic reactors, pipes, and conduits. Accordingly, efforts have been made to stabilize olefin metathesis product mixtures against double bond isomerization and decomposition resulting from metal contaminants.

H. D. Maynard and R. H. Grubbs disclose in *Tetrahedron Letters*, 40 (1999), 4137-4140, purification of ring-closing metathesis products of metathesis reactions utilizing a ruthenium catalyst. The purification involves treating the metathesis product mixture with a water-soluble phosphine, specifically, tris(hydroxymethyl)phosphine, followed by extraction with water so as to remove ruthenium into an aqueous phase. Disadvantageously, this method reduces the concentration of ruthenium by only one order of magnitude when an excess of 10 equivalents of water soluble phosphine is employed.

Leo A Paquette et al. discloses in *Organic Letters*, 2 (9) (2000), 1259-1261 the addition of lead tetraacetate to ring-closing metathesis product mixtures followed by filtration over silica gel to remove the colored ruthenium catalysts and impurities. The method teaches reduction of ruthenium residues by a factor of about 56. Disadvantageously, this method requires the use of lead tetraacetate under anaerobic conditions and thereafter a separate filtration step.

Yu Mi Ahn et al. discloses in *Organic Letters*, 3 (9) (2001), 1411-1413, a method of similar efficiency that involves treating the crude olefin metathesis product mixtures with triphenylphosphine oxide or dimethyl sulfoxide, followed by column chromatography on silica gel. Disadvantageously, this method employs a large quantity of triphenylphosphine oxide or dimethyl sulfoxide, both of which increase costs and add recovery steps to any commercial plan.

An earlier reference, U.S. Pat. No. 6,156,692 (filed 1997), drawn to a ring-opening polymerization of a cyclic olefin, discloses work-up of a crude polyolefin product over Darco™ brand charcoal. The reference teaches decolorizing the polymer, but does not address the problem of stabilizing an olefin metathesis product mixture against double bond isomerization and decomposition. Moreover, the final concentration of ruthenium in the polymer product (86 parts per million to 0.047 weight percent) is not sufficiently low to provide stabilization against double bond migration and decomposition.

In view of the prior art, it would be desirable to discover an improved method of stabilizing an olefin metathesis product mixture. It would also be desirable to discover an improved method of removing metals from olefin metathesis product mixtures. It would be more desirable if the improved method did not employ expensive reagents that require recovery. It would be even more desirable if the improved method did not employ large quantities of solvents or fluids that also increase costs and require recovery and recycle. It would be most desirable if the improved method could reduce the concentration of metal(s) in metathesis product mixtures more efficiently than prior art methods. At a high efficiency of metal removal, olefin metathesis product mixtures are more likely to be stabilized against double bond isomerization and chemical and thermal decomposition.

SUMMARY OF THE INVENTION

In a first aspect this invention provides for a novel method of stabilizing an olefin metathesis product mixture. The method comprises (a) contacting an olefin metathesis product mixture, comprising one or more olefins obtained in a metathesis process, a metathesis catalyst comprising a catalytic metal, optionally, one or more metathesis catalyst degradation products, and optionally, one or more metals derived from sources other than the catalyst and catalyst degradation products, with an absorbent; or (b) subjecting the olefin metathesis product mixture to a first distillation to remove substantially volatiles and lights, and thereafter, subjecting bottoms from the first distillation to a second distillation; the (a) adsorbent or (b) distillation method being conducted under conditions sufficient to remove the metal(s) to a concentration sufficient to stabilize the product mixture. Optionally, the olefin metathesis product mixture may additionally comprise one or more metathesis reaction by-products, one or more unconverted reactant olefins, one or more solvents, or a combination thereof. The olefin metathesis catalyst shall comprise, in addition to the catalytic metal, a catalytically-active combination of one or more ligands. The metathesis catalyst degradation products shall include ligand degradation products, complexes of the catalytic metal with one or more ligand degradation products, or complexes of catalytic metal with a catalytically-inactive combination of ligands. Additionally, metals may be derived from sources other than the metathesis catalyst, such as, added promoter elements and metals leached out of catalyst supports, other heterogeneous catalysts, reactors, pipes, and conduits.

The novel process of this invention beneficially stabilizes a metathesis product mixture, preferably, against double bond isomerization and undesirable chemical and thermal decomposition. For the purposes of this invention, the term "stabilize" shall be taken to mean that the product mixture is rendered more resistant to isomerization and chemical and thermal decomposition, as compared with the metathesis product mixture prior to treatment with adsorbent or distillation as disclosed herein. For the purposes of this invention, the term "isomerization" shall be defined as the migration of a carbon-carbon double bond, either in a product olefin or a reactant olefin, from one carbon-carbon pair to another carbon-carbon pair. The term "thermal decomposition" shall be defined as the heat-induced break-down of compound, herein the product olefin(s) and optionally the reactant olefin(s), into one or more molecular fragments or residues. The term "chemical decomposition" shall include any undesirable chemical transformation of a compound, herein the product olefin(s) and optionally the reactant olefin(s), to form a by-product. Accordingly, the novel stabilization method of this invention beneficially reduces the chances of such detrimental processes and allows for storage of product mixtures at higher temperatures and for longer periods of time. Moreover, the novel stabilization method also allows for the subsequent separation of products, for example, by distillation, at higher temperatures. Losses in target product olefins and raw material olefins are reduced. In contrast to prior art methods, the adsorbent method of this invention advantageously involves one process step and uses inexpensive and readily accessible materials. Additionally, the process of this invention is easily integrated into the work-up of a metathesis product mixture. The selection of adsorbent method or distillation method offers flexibility depending, for example, upon the particular plant design and economics. Moreover, the stabilization method of this invention typically does not introduce additional metals or compounds into the olefin metathesis product mixture that might be difficult to separate or might induce adverse effects.

In a second aspect, this invention pertains to a novel stabilized olefin metathesis product composition comprising one or more olefins produced in a metathesis process, the composition having a total concentration of metal(s) of less than about 30 parts per million (ppm) by weight, based on the weight of the olefin metathesis product mixture. Optionally, the olefin metathesis product composition may additionally comprise one or more unconverted reactant olefins, one or more olefin metathesis by-products, one or more ligands, one or more solvents, or a combination thereof.

Olefins prepared by metathesis find utility as starting materials for the production of polyolefins, polyester polyols, polyester polyamines, and polyester polyepoxides, all of which find further utility in the manufacture of polymeric thermoset resins. Stabilized olefin metathesis products are more likely to have greater stability and a longer shelf life without undesirable isomerization and by-product formation.

In a third aspect this invention provides for two novel methods of removing catalytic and non-catalytic metals from an olefin metathesis product mixture. In one aspect, the invention comprises contacting an olefin metathesis product mixture comprising one or more olefins produced in a metathesis process and one or more metals, with an adsorbent under conditions sufficient to reduce the metals to a total concentration of less than about 30 parts per million (ppm) by weight, based on the weight of the olefin metathesis product mixture. In another aspect, the invention comprises subjecting an olefin metathesis product mixture to a first distillation to remove substantially volatiles and lights, and thereafter, subjecting bottoms from the first distillation to a second distillation so as to separate the olefin metathesis products from the metal(s); the distillations being conducted under conditions sufficient to reduce the metal(s) to a concentration of less than about 30 ppm by weight, based on the weight of the olefin metathesis product mixture.

In this third aspect, the invention provides for a process of removing the metals present in an olefin metathesis product mixture to a low concentration, namely, a total concentration of less than about 30 ppm by weight. The process is effected in one simple step with inexpensive, readily obtainable adsorbents, or alternatively, with distillation. Beneficially, a high efficiency of metal removal is achieved, as compared with prior art methods. In preferred embodiments employing specific carbon adsorbents, metal removal is highly efficient resulting in a total metal concentration in the parts per billion range. The removal of metals from the olefin metathesis product mixture beneficially enhances product stability against double bond isomerization and thermal and chemical decomposition, as well as providing a product of higher purity. Moreover, the metals removed by the novel process can be recovered and reprocessed.

DETAILED DESCRIPTION OF THE INVENTION

Generally, olefin metathesis product mixtures are obtained by contacting a first reactant olefin with a second reactant olefin or a reactant alkyne in the presence of a metathesis catalyst under reaction conditions sufficient to prepare one or more unsaturated products that are different from the reactant olefins. The metathesis catalyst generally comprises one or more catalytic metals and a catalytically active combination of one or more ligands. During metathesis, the catalyst may degrade in part, for example, when the ligand reacts to form ligand degradation products or when the catalytic metal binds to ligand degradation products. The metathesis catalyst and metathesis catalyst degradation products provide a source of metals that can destabilize the olefin metathesis product mixture. Destabilization can take the form of double bond isomerization to yield isomers different from the target or reactant isomer(s), and/or chemical and thermal decomposition to yield undesirable by-products of lower commercial value. Additionally, the olefin metathesis product mixture may contain destabilizing metals derived from extraneous sources, including metallic promoters added to facilitate the metathesis process itself or metals leached into the metathesis reaction from a heterogeneous catalyst, catalyst support, or a reactor, pipes, and conduits.

In the novel process of this invention an olefin metathesis product mixture is beneficially stabilized, preferably, against double bond isomerization and thermal and chemical decomposition. The novel process comprises (a) contacting an olefin metathesis product mixture, comprising one or more olefins obtained in a metathesis process, a metathesis catalyst comprising one or more catalytic metals, optionally, one or more catalyst degradation products, and optionally, one or more metals derived from sources other than the catalyst and catalyst degradation products, with an adsorbent, or (b) subjecting the olefin metathesis product mixture to a first distillation to remove substantially volatiles and lights, and thereafter, subjecting bottoms from the first distillation to a second distillation; the (a) adsorbent or (b) distillation method being conducted under conditions sufficient to remove the metal(s) to a concentration sufficient to stabilize the metathesis product mixture, as compared with the untreated product mixture. This invention is not limited to any particular form or valence of the metal(s). Elemental metal(s) or metallic ions are all suitably removed in the process of this invention.

In another aspect, this invention provides for a novel, stabilized olefin metathesis product composition comprising one or more olefins produced in an olefin metathesis process, the composition having a total concentration of metal(s) of less than about 30 parts per minion (ppm) by weight, based on the weight of the olefin metathesis product mixture.

In yet another aspect, this invention provides for novel methods of reducing the concentration of metals in an olefin metathesis product mixture. In one aspect, the process comprises contacting an olefin metathesis product mixture comprising one or more olefins produced in a metathesis process and one or more metals, with an adsorbent under conditions sufficient to reduce the concentration of metal(s) to less than about 30 ppm by weight, based on the weight of the olefin metathesis product mixture. In another aspect, the process comprises subjecting the olefin metathesis product mixture comprising one or more olefins produced in a metathesis process and one or more metals to a first distillation to remove substantially volatiles and lights, and thereafter, subjecting bottoms from the first distillation to a second distillation; the distillation method being conducted under conditions sufficient to reduce the metal(s) to a concentration less than about 30 ppm by weight, based on the weight of the product mixture.

In one preferred embodiment of the aforementioned inventions, the metal comprises ruthenium, molybdenum, tungsten, rhenium, or a combination thereof.

In another preferred embodiment of the aforementioned invention, the adsorbent comprises carbon, more preferably, a wood carbon. In this preferred embodiment, the removal of metathesis catalyst and metathesis catalyst degradation products is highly efficient, as compared with prior art methods; for example, on treatment with the preferred wood carbon, metals are reduced to a total concentration in the parts per billion range.

In another preferred embodiment of this invention, the distillation method comprises subjecting an olefin metathesis product mixture to a first distillation under conditions sufficient to remove substantially volatiles and lights; and thereafter subjecting bottoms from the first distillation to a short path wiped-film evaporation under conditions sufficient to reduce metal(s) in the metathesis product mixture to a concentration of less than about 100 parts per billion (ppb) by weight.

In the inventions described herein, the starting metathesis product composition can be obtained from any metathesis process, including for example, homo-metathesis processes between two reactant olefins of identical chemical composition; cross-metathesis processes between two reactant olefins of different chemical composition; metathesis processes between similar or different acyclic olefins to product acyclic metathesized olefin products; ring-opening polymerization metathesis processes to form linear, unsaturated polymers; ring-closing metathesis processes to form unsaturated ring compounds; and cross-metathesis processes of an alkene and an alkyne to form a conjugated 1,3-diene. A preferred metathesis process involves the metathesis of a long chain unsaturated olefin, such as methyl oleate or oleic acid, with a short chain olefin, preferably, a $C_{2-8}$ olefin, more preferably, ethylene or propylene, to form one or more intermediate-chain olefins, such as 1-decene or methyl 9-decenoate.

The generation of olefin metathesis product mixtures via olefin metathesis processes is well-documented in the art, as noted for example, by K. J. Ivin and J. C. Mol, *Olefin Metathesis and Metathesis Polymerization*, Academic Press, San Diego, 1997, as well as by M. R. Buchmeiser, *Chemical Reviews*, 2000, 100, 1565-1604. Reactant olefins can include any hydrocarbon or substituted hydrocarbon having at least one olefinic carbon-carbon double bond. Preferred olefins contain from 2 to about 50 carbon atoms, more preferably, from 2 to about 30 carbon atoms. The reactant olefins can be the same or different, and they can be each independently acyclic or cyclic. The reactant olefins can each have two or more double bonds. The substituents on the reactant olefins may include any substituent that does not inhibit the desired metathesis process. Non-limiting examples of suitable substituents include alkyl moieties, preferably $C_{1-10}$ alkyl moieties, including for example methyl, ethyl, propyl, butyl, and the like; cycloalkyl moieties, preferably, $C_{4-8}$ cycloalkyl moieties, including for example, cyclopentyl and cyclohexyl;

monocyclic aromatic moieties, preferably, $C_6$ aromatic moieties, that is, phenyl; arylalkyl moieties, preferably, $C_{7-16}$ arylalkyl moieties, including, for example, benzyl; and alkylaryl moieties, preferably, $C_{7-16}$ alkylaryl moieties, including, for example, tolyl ethylphenyl, xylyl and the like; as well as ether, acyl, hydroxy, halo (preferably, chloro and bromo), nitro, carboxylic acid, ester, and amide moieties. Non-limiting examples of suitable reactant olefins include ethylene, propylene, butylene, pentene, hexene, heptene, octene, nonene, decene, dodecene, cyclopentene, cyclohexene, cyclooctene, butadiene, octadiene, norbornene, dicyclopentadiene, cyclooctadiene, acrylamide, methyl acrylate; unsaturated fatty acids, such as 3-hexenoic (hydrosorbic), trans-2-heptenoic, 2-octenoic, 2-nonenoic, cis- and trans-4-decenoic, 9-decenoic (caproleic), 10-undecenoic (undecylenic), cis-4-dodecenoic (linderic), tridecenoic, cis-9-tetradecenoic (myristoleic), pentadecenoic, cis-9-hexadecenoic (cis-9-palmitoleic), trans-9-hexadecenoic (trans-9-palmitoleic), 9-heptadecenoic, cis-6-octadecenoic (petroselinic), trans-6-octadecenoic (petroselaidic), cis-9-octadecenoic (oleic), trans-9-octadecenoic (elaidic), cis-11-octadecenoic, trans-11-octadecenoic (vaccenic), cis-5-eicosenoic, cis-9-eicosenoic (gadoleic), cis-11-docosenoic (cetoleic), cis-13-docosenoic (erucic), trans-13-docosenoic (brassidic), cis-15-tetracosenoic (selacholeic), cis-17-hexacosenoic (ximenic), and cis-21-triacontenoic (lumequeic) acids, as well as 2,4-hexadienoic (sorbic), cis-9-cis-12-octadecadienoic (linoleic), cis-9-cis-12-cis-15-octadecatrienoic (linolenic), eleostearic, 12-hydroxy-cis-9-octadecenoic (ricinoleic), cis-5-docosenoic, cis-5,13-docosadienoic, and like acids.

Unsaturated fatty acid esters are also suitable metathesis reactants. The alcohol segment of the fatty acid ester can be any monohydric, dihydric, or polyhydric alcohol capable of condensation with an unsaturated fatty acid to form the ester. In seed oils the alcohol segment is glycerol, a trihydric alcohol. If desired, the glycerides can be converted via transesterification to fatty acid esters of lower alkanols, which may be more readily separated or suitable for downstream chemical processing. Typically, the alcohol used in transesterification contains at least one carbon atom. Typically, the alcohol contains less than about 15 carbon atoms, preferably, less than about 12 carbon atoms, more preferably, less than about 10 carbon atoms, and even more preferably, less than about 8 carbon atoms. The carbon atoms in the alcohol segment may be arranged in a straight-chain or branched structure, and may be substituted with a variety of substituents, such as those previously disclosed hereinabove in connection with the reactant olefin, including the aforementioned alkyl, cycloalkyl, monocyclic aromatic, arylalkyl, alkylaryl, hydroxyl, halo, nitro, carboxylic acid, ether, ester, acyl, and amide substituents. Preferably, the alcohol segment of the unsaturated fatty acid ester is glycerol or a straight-chain or branched $C_{1-8}$ alkanol. Most preferably, the alcohol is a $C_{1-4}$ alkanol, suitable examples of which include methanol ethanol, and propanol.

In a more preferred embodiment, one reactant olefin is a $C_{6-30}$ unsaturated fatty acid or unsaturated fatty acid ester, most preferably, oleic acid or an ester of oleic acid. The second reactant olefin is more preferably a "lower olefin," that is, a $C_{2-5}$ olefin, such as, ethylene, propylene, 1-butene, 2-butene, butadiene, pentenes, or mixtures thereof. Even more preferably, the second reactant olefin is ethylene or propylene, most preferably, ethylene.

Metathesis process conditions are also well documented in the art. (See references cited hereinabove.) The reactant olefins may be fed to the metathesis process in any operable quantities. Depending upon the particular reactants and desired products, it may be beneficial to minimize the homo-metathesis of the reactant olefins. One skilled in the art will know how to choose the relative amounts of reactant olefins, and if desired, how to minimize homo-metathesis reactions. Typically, the ratio of a first reactant olefin to a second reactant olefin is at least about 0.8/1. The following molar ratios may be used as a guideline for the metathesis of preferred long-chain unsaturated fatty acids or fatty acid esters with preferred lower olefins. Typically, the molar ratio of lower olefin to total unsaturated fatty acids or fatty acid esters is greater than about 0.8/1.0, preferably, greater than about 0.9/1.0. Typically, the molar ratio of lower olefin to total unsaturated fatty acids or fatty acid esters is less than about 5/1, and preferably, less than about 3/1. When the lower olefin is ethylene, homo-metathesis is not problematical, and the molar ratio of ethylene to unsaturated fatty acid or fatty acid ester can range up to about 20/1.0. More preferably, when ethylene is employed, the molar ratio is less than about 10/1.0.

The reactant olefin is typically provided to the metathesis process in a neat liquid phase without a solvent, because the use of a solvent may increase recycle requirements and costs. Optionally, however, a solvent may be employed. When a solvent is used, the metathesis olefin product composition further contains the solvent, which may be subsequently recovered and recycled to the metathesis process. Non-limiting examples of suitable solvents include aromatic hydrocarbons, such as benzene, toluene, and xylenes; chlorinated aromatic hydrocarbons, preferably chlorinated benzenes, such as chlorobenzene and dichlorobenzene; alkanes, such as pentane, hexane, and cyclohexane; ethers, such as diethyl ether and tetrahydrofuran; and chlorinated alkanes, such as methylene chloride and chloroform. Any operable amount of solvent is acceptable. Generally, the concentration of each reactant olefin in the solvent is greater than about 0.05 M, preferably, greater than about 0.5 M, but typically, less than about the saturation concentration, and preferably, less than about 5.0 M.

Lower olefins, such as ethylene, propylene, and butenes, can be fed to the metathesis as an essentially pure gas or, optionally, diluted with a gaseous diluent. As the gaseous diluent, any substantially inert gas may be used, suitable examples of which include, without limitation, helium, neon, argon, nitrogen, and mixtures thereof. If a gaseous diluent is used, then the concentration of lower olefin in the diluent may suitably range from greater than about 5 mole percent, and preferably, greater than about 10 mole percent, to typically less than about 90 mole percent lower olefin, based on the total moles of lower olefin and gaseous diluent. Typically, oxygen is excluded from the metathesis process, so as to avoid undesirable side-reactions with the metathesis catalyst and its component parts (metal and ligands) as well as with reactant and product olefins.

As a further option, a stabilizing ligand may be added to the metathesis process. The stabilizing ligand can comprise any molecule or ion that promotes catalyst stability in the metathesis process, as measured, for example, by increased activity or extended catalyst lifetime. Non-limiting examples of stabilizing ligands include tri(alkyl)phosphines, such as tricyclohexylphosphine, tricyclopentylphosphine, and tributylphosphine; tri(aryl)phosphines, such as tri(phenyl)phosphine and tri(methylphenyl)phosphine; alkyldiarylphosphines, such as cyclohexyldiphenylphosphine; dialkylarylphosphines, such as dicyclohexylphenylphosphine; ethers, such as anisole; phosphine oxides, such as triphenylphosphine oxide; as well as phosphinites, phosphonites, phosphoramidites, pyridines, and any combination of the aforementioned compounds. Preferably, the stabilizing ligand is selected from the aforementioned phosphines, and more preferably, is tri(cyclohexyl)phosphine or tri(phenyl) phosphine. The quantity of stabilizing ligand can vary depending upon the specific catalyst employed and its specific ligand components. Typically, the molar ratio of stabilizing ligand to catalyst is greater than about 0.05/1, and preferably, greater than about 0.5/1. Typically, the molar ratio of stabilizing ligand to catalyst is less than about 2.0/1, and preferably, less than about 1.5/1.

The metathesis catalyst can comprise any catalyst that is capable of facilitating a metathesis process. Many metathesis catalysts are known in the art, representative examples of which are disclosed in WO 93/20111, U.S. Pat. No. 5,312,940, WO 96/04289; and by J. Kingsbury et al in *Journal of the American Chemical Society*, 121 (1999), 791-799; as well as in co-pending International Patent Application Serial No. PCT/US 02/05894 (Attorney Docket No. 61071A), filed on Feb. 27, 2002, in the name of Thomas E. Newman, Cynthia Rand, Robert Maughon, Kenneth Burdett, Donald Morrison, and Eric Wasserman; the aforementioned references being incorporated herein by reference. The preferred metathesis catalyst comprises a catalytic metal selected from ruthenium, molybdenum, tungsten, rhenium or a mixture thereof; more preferably, ruthenium, molybdenum, rhenium, or a mixture thereof; and most preferably, ruthenium. Non-limiting examples of suitable ruthenium catalysts include dichloro-3, 3-diphenylvinylcarbene-bis(tricyclohexylphosphine)ruthenium (II), bis(tricyclohexylphosphine)benzylidene ruthenium dichloride, bis(tricyclohexylphosphine)benzylidene ruthenium dibromide, tricyclohexylphosphine[1,3-bis(2,4,6-trimethylphenyl)-4,5-dihydroimidazol-2-ylidene][benzylidene]ruthenium dichloride, tricyclohexylphosphine[1,3-bis(2,4,6-trimethylphenyl)-4,5-dihydroimidazol-2-ylidene][benzylidene]ruthenium dibromide, and tricyclohexylphosphine[1,3-bis(2,4,6-trimethylphenyl)-4,5-dihydroimidazol-2-ylidene][benzylidene]ruthenium diiodide. Non-limiting examples of suitable molybdenum, rhenium, and tungsten catalysts include $MoO_3$/silica, 2,6-diisopropylphenyl-imidoneophylidenemolybdenum (VI) bis (hexafluoro-t-butoxide), $Re_2O_7$/alumina/$R_4Sn$, $ReO_7$/silica-alumina/$R_4Sn$, $Re_2O_7$/$B_2O_3$-alumina/$R_4Sn$, $WCl_6$/$R_4Sn$, wherein in the aforementioned formulas each R is independently selected from alkyl and aryl moieties and substituted derivatives thereof, preferably, $C_{1-20}$ alkyl and $C_{6-20}$ aryl moieties.

Most preferably, the ruthenium metathesis catalyst is selected from the group consisting of dichloro-3,3-diphenylvinylcarbene-bis(tricyclohexylphosphine)ruthenium (II), bis(tricyclohexylphosphine)benzylidene ruthenium dichloride, tricyclohexylphosphine[1,3-bis(2,4,6-trimethylphenyl)-4,5-dihydroimidazol-2-ylidene][benzylidene]ruthenium (IV) dichloride, tricyclohexylphosphine[1,3-bis(2,4,6-trimethylphenyl)-4,5-dihydroimidazol-2-ylidene][benzylidene]ruthenium (IV) dibromide, tricyclohexylphosphine[1,3-bis(2,4,6-trimethylphenyl)-4,5-dihydroimidazol-2-ylidene][benzylidene]ruthenium (IV) diiodide, and the chelated ruthenium complexes represented by the following formula I:

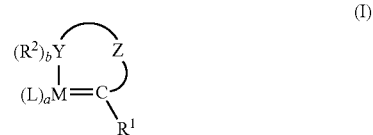

In formula I, M is Ru; each L is independently selected from neutral and anionic ligands in any combination that balances the bonding and charge requirements of M; a is an integer, preferably from 1 to about 4, which represents the total number of ligands L; $R^1$ is selected from hydrogen, straight-chain or branched alkyl, cycloalkyl, aryl and substituted aryl radicals; Y is an electron donor group of an element from Group 15 or 16 of the Periodic Table, (as referenced by the IUPAC in *Nomenclature of Inorganic Chemistry: Recommendations* 1990, G. J. Leigh, Editor, Blackwell Scientific Publications, 1990); Y being more preferably O, S, N, or P; each $R^2$ is independently selected from hydrogen, alkyl, cycloalkyl, aryl, and substituted aryl radicals sufficient to satisfy the valency of Y, preferably such that Y is formally neutral; b is an integer, preferably 0 to about 2, representing the total number of $R^2$ radicals; and Z is an organic diradical that is bonded to both Y and the carbene carbon (C) so as to form a bidentate ligand, which ligand in connection with the M atom forms a ring of from about 4 to about 8 atoms. More preferably, each L in formula I is independently selected from the group consisting of halides, most preferably, fluoride, chloride, bromide, and iodide; cyanide, thiocyanate, phosphines of the formula $PR^3_3$, amines of the formula $NR^3_3$, water and ethers of the formula $OR^3_2$, thioethers of the formula $SR^3_2$, and ligands having the formulas II and III hereinafter:

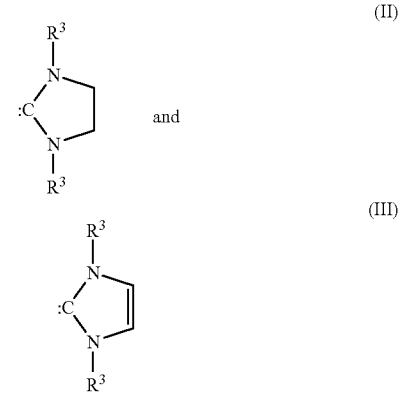

wherein each $R^3$ in any of the aforementioned formulas is independently selected from the group consisting of hydrogen, alkyl, preferably, $C_{1-15}$ alkyl; cycloalkyl, preferably, $C_{3-8}$ cycloalkyl; aryl, preferably, $C_{6-15}$ aryl, and substituted aryl, preferably $C_{6-15}$ substituted aryl, radicals. Mixtures of any of the aforementioned ligands L may be employed in any given species of formula I. More preferably, $R^1$ in Formula I is selected from the group consisting of hydrogen, $C_{1-15}$ alkyl, $C_{3-8}$ cycloalkyl, and $C_{1-15}$ aryl radicals. More preferably, each $R^2$ is independently selected from the group consisting of $C_{1-15}$ alkyl $C_{3-8}$ cycloalkyl, and $C_{6-5}$ aryl radicals. Preferably, Z is selected from the following diradicals: ethylene (IV), vinylene (V), phenylene (VI), substituted vinylenes (VII), substituted phenylenes (VIII), naphthylene (IX), substituted naphthylenes (X), piperazindiyl (XI), piperidiyl (XII)

(IV)

(V)

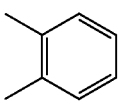
(VI)

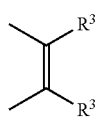
(VII)

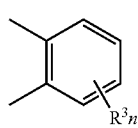
(VIII)

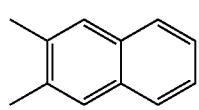
(IX)

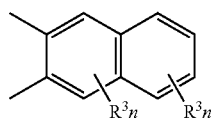
(X)

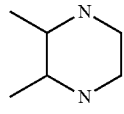
(XI)

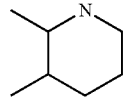
(XII)

wherein each $R^3$ may be, as noted above, selected from hydrogen, alkyl, preferably, $C_{1-15}$ alkyl; cycloalkyl, preferably, $C_{3-8}$ cycloalkyl; and aryl preferably, $C_{6-15}$ aryl radicals; and wherein each n is an integer from 1 to about 4. The most preferred embodiment of formula I is represented by formula XIII:

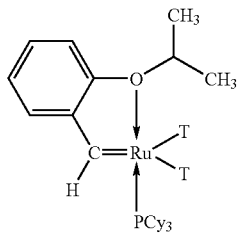
(XIII)

wherein each T is independently selected from Cl and Br, and $PCy_3$ is tricyclohexylphosphine.

Although the metathesis catalyst is preferably a homogeneous catalyst dissolved in the metathesis reaction fluid, the catalyst may be provided in a heterogeneous form bound to or deposited on any conventional catalyst support. Such supports are known to the skilled artisan, and include, for example, silica, alumina, silica-aluminas, aluminosilicates, titania, titanosilicates, carbon, and reticulated cross-linked polymeric resins, such as reticulated cross-linked polystyrenes. If a catalyst support is used, the metathesis catalyst may be loaded onto the catalyst support in any amount, provided that the metathesis process proceeds to the targeted metathesis products. Generally, the catalyst loading on the support is greater than about 0.01 weight percent catalytic metal, and preferably, greater than about 0.05 weight percent catalytic metal, based on the total weight of catalyst plus support. Generally, the loading is less than about 20 weight percent catalytic metal, and preferably, less than about 10 weight percent catalytic metal, based on the total weight of the catalyst and support.

Metathesis process conditions are well documented in the art, as noted in the above-cited references. Typical process conditions are summarized hereinbelow; but the inventions disclosed herein should not be bound or limited in any manner by the following statements. Other metathesis process conditions may be suitable, depending upon the particular reactants and catalyst employed and upon the products targeted. Generally, the process is conducted at a temperature greater than about 0° C., preferably, greater than about 15° C., and more preferably, greater than about 25° C. Generally, the metathesis process is conducted at a temperature less than about 80° C., preferably, less than about 50° C., and more preferably, less than about 35° C. The total pressure, including reactant olefins and gaseous diluent, is typically greater than about 5 psig (34.5 kPa), preferably, greater than about 10 psig (68.9 kPa), and more preferably, greater than about 45 psig (310 kPa). Typically, the total pressure is less than about 500 psig (2,758 kPa), preferably, less than about 250 psig (1,723 kPa), and more preferably, less than about 100 psig (690 kPa). If the metathesis process is conducted in a batch reactor, the ratio of moles of olefin feedstock to moles of metathesis catalyst will typically be greater than about 10:1, preferably, greater than about 50:1, and more preferably, greater than about 100:1. The molar ratio of olefin feedstock to metathesis catalyst will be typically less than about 10,000,000:1, preferably, less than about 1,000,000:1, and more preferably, less than about 500,000:1. If the process is conducted in a continuous flow reactor, then the weight hourly space velocity, given in units of grams metathesis feedstock per gram catalyst per hour ($h^{-1}$) determines the relative quantity of reactant olefins to catalyst employed, as well as the residence time of the olefin feedstock in the reactor. Accordingly, the weight hourly space velocity of the reactant olefin feedstock is typically greater than about 0.04 g per g catalyst per hour (h$^{-1}$), and preferably, greater than about 0.1 h$^{-1}$. The weight hourly space velocity of the olefin reactant feedstock is typically less than about 100 h$^{-1}$, and preferably, less than about 20 h$^{-1}$. The flows of olefin reactants are typically adjusted to produce the desired ratio of first reactant olefin to second reactant olefin.

When the metathesis process is conducted as described hereinabove, then a metathesis product mixture is obtained that contains one or more product olefins, a metathesis catalyst comprising catalytic metal and one or more ligands; optionally, one or more catalyst degradation products; optionally, one or more unconverted olefin reactants; and optionally one or more metals obtained from sources other than the catalyst and catalyst degradation products including, for example, iron, nickel copper, zinc, cobalt, chromium, lithium, sodium, potassium, magnesium, calcium, and mixtures thereof. Other optional components of the metathesis product mixture include one or more metathesis by-products, one or more solvents, and one or more stabilizing ligands. The metathesis product olefins may include, for example, unsubstituted and substituted acyclic olefins, unsubstituted and substituted cyclic olefins, polyolefin polymers, and conjugated 1,3-dienes, providing at least one product olefin is different from the reactant olefins. The product olefins may include monoolefins, diolefins, and polyolefins, and substituted derivatives thereof. Suitable substituents have been named already in connection with the substituted reactant olefins. Preferably, the acyclic olefin is a $C_{2-20}$ acyclic olefin. Preferably, the cyclic olefin is a $C_{4-8}$ cyclic olefin. In a preferred embodiment of the invention, the metathesis product olefin is a $C_{2-20}$ α-olefin, such as 1-decene, or a $C_{2-20}$ α,ω-unsaturated ester or acid, such as methyl 9-decenoate.

It is to be noted that typically metathesis product mixtures contain the catalytic metal(s) in a concentration greater than about 1 part per million (ppm), more typically, greater than about 30 ppm by weight, based on the weight of the product mixture. Typically, the concentration of catalytic metal in the metathesis product mixture is less than about 500 ppm, preferably, less than about 100 ppm, by weight.

The metathesis product mixture may be separated by conventional methods known to those skilled in the art, for example, distillation, extraction, precipitation, crystallization, membrane separation, and the like. Since metals present in the product mixture can detrimentally induce double-bond isomerization and thermal and chemical decomposition, the process of this invention addresses the need to remove catalytic metals and other metals present from extraneous sources. While the metals can be removed any time after the metathesis reaction is complete, it is preferable to remove the metals early on, that is, soon after the metathesis reaction is finished, and preferably, prior to effecting separation at elevated temperature or storage for long periods of time.

In accordance with the process of this invention, the metathesis product mixture may be (a) contacted with an adsorbent, or (b) subjected to distillation under process conditions sufficient to remove metals to a concentration sufficient to stabilize the mixture, relative to the starting metathesis product mixture that has not been stabilized by the method described herein (crude mixture). Typically, after treatment by method (a) or (b), the total concentration of metal(s) is less than about 30 parts per million by weight, based on the weight of the olefin metathesis product mixture. Preferably, the total concentration of metal(s) is reduced to less than about 15 parts per million, more preferably, to less than about 5 parts per million, even more preferably, to less than about 1 part per million. In most preferred embodiments of the invention, the total concentration of metal(s) is reduced to less than about 0.3 parts per million (300 parts per billion), based on the weight of metathesis product mixture. The reduced concentration of metal(s), however, is typically, greater than about 0 parts per trillion, and more typically, greater than about 1 part per billion, based on the weight of metathesis product mixture.

Any adsorbent that is capable of stabilizing the metathesis product mixture may be employed in the process of this invention. Non-limiting examples of suitable adsorbents include without limitation carbons, silica gels, diatomaceous earths, clays, reticular cross-linked ion-exchange resins, aluminas, silica-aluminas, and mixtures thereof. Suitable clays include, without limitation, montmorillonite, bentonite, and kaolin clays. Suitable carbons include, without limitation, wood, and coconut carbons. Suitable reticular cross-linked ion-exchange resins include, without limitation, reticular cross-linked ionically-functionalized polystyrene resins. If silica such as silica gel is used, then preferably, the silica or silica gel is used exclusive of other treatments, preferably, exclusive of treatments with lead tetraacetate, tris(hydroxymethyl)phosphine, triphenylphosphine oxide, dimethyl sulfoxide, or mixtures thereof. Preferably, the adsorbent is selected from carbons, clays, reticular cross-linked ion-exchange resins, aluminas, silica-aluminas, and mixtures thereof. More preferably, the adsorbent is carbon, even more preferably, a wood carbon. Most preferably, the carbon adsorbent is a Westvaco Nuchar™ brand wood carbon.

Any weight ratio of adsorbent to metathesis product mixture can be employed, provided that the mixture is stabilized. Generally, the adsorbent is used in a quantity greater than about 0.1 weight percent, preferably, greater than about 1 weight percent, based on the weight of the metathesis product mixture. Generally, the adsorbent is used in a quantity less than about 20 weight percent, preferably, less than about 10 weight percent, based on the weight of the metathesis product mixture.

The contacting of the metathesis product mixture with the adsorbent can be effected in any conventional manner, for example, by slurrying the product mixture with the adsorbent followed by filtration, or by passing the product mixture through a fixed column of the adsorbent. If the metathesis product mixture is not sufficiently fluid at the contacting temperature, the product mixture may be dissolved in a suitable solvent for ease of contacting with the adsorbent. Any thermally and chemically stable solvent having acceptable solubility may be used. Non-limiting examples of suitable solvents include aromatic hydrocarbons, such as benzene, toluene, and xylenes; chlorinated aromatic hydrocarbons, preferably chlorinated benzenes, such as chlorobenzene and dichlorobenzene; alkanes, such as pentane, hexane, and cyclohexane; ethers, such as diethyl ether and tetrahydrofuran; and chlorinated alkanes, such as methylene chloride and chloroform. The contacting temperature and pressure may vary depending upon the specific operational design, product mixture, and adsorbent selected. Usually, the contacting temperature is greater than about −10° C., preferably, greater than about 5° C. Usually, the contacting temperature is less than about 70° C., preferably, less than about 50° C. The pressure may range from subatmospheric to superatmospheric, with a preferred range from about atmospheric to about 100 psig (689.5 kPa). The contacting time can also vary depending upon the specifics of the product mixture and adsorbent selected. Typically, in a slurry or batch process the contacting time is greater than about 15 minutes. Preferably, the contacting time is less than about 24 hours, more preferably, less than about 12 hours, even more preferably, less than about 6 hours, and most preferably, less than about 4 hours. Typically, in a continuous flow, fixed bed process, the weight hourly space velocity, given in units of grams metathesis product mixture per gram adsorbent per hour ($hr^{-1}$), is typically greater than about 0.01 $hr^{-1}$, preferably, greater than about 0.1 $hr^{-1}$. Typically, the weight hourly space velocity is less than about 10 $hr^{-1}$, and preferably, less than about 5 $hr^{-1}$. Otherwise, no special procedures are required for the process of this invention. The process may be conducted under air, provided that air/oxygen does not react with the olefinic products or reactants.

In an alternative embodiment of this invention, metal(s) can be removed from an olefin metathesis product mixture by distillation to yield stabilized metathesis product mixtures having the low concentrations of metal(s) described hereinbefore. In the distillation method of this invention, the metathesis product mixture is subjected to a first distillation to remove substantially lights or volatiles; and thereafter, the bottoms from the first distillation are subjected to a second distillation in a short-path wiped film evaporator to reduce the metal(s) concentration to less than about 30 ppm, and preferably, less than about 100 ppb. Lights removal, as a first stage, appears to be important to the success of reducing metal(s) to a final concentration of less than about 100 ppb. If substantial amounts of lights are present in the second distillation, then entrainment of the metals into the olefin distillate may be unavoidable. After lights and volatiles removal the concentration of metal(s) achieved in the distillate at the second stage is generally less than about 100 ppb, and preferably, less than about 75 ppb by weight. The phrase "to remove substantially lights and volatiles" means that greater than about 75 percent by weight, preferably, greater than about 85 percent by weight, and more preferably, greater than about 90 percent by weight, of the lights and volatiles are removed, based on the weight of the olefin metathesis product mixture fed to the first distillation. Lights and volatiles primarily include metathesis solvent and may also include lower olefin and volatile metathesis by-products.

The first distillation step may be conducted in any suitable equipment, so long as the volatiles and lights are substantially removed without unacceptable loss of target olefin products. Equipment suitably employed includes, without limitation, a distillation tower, stripper, falling film evaporator, wiped film evaporator, or short-path wiped film evaporator, all known to those of skill in the art. The actual equipment chosen will depend upon the operating temperature and operating pressure required to remove the volatiles and lights, as well cost considerations, equipment availability, and consideration of the properties (stability, volatility, etc.) of the specific components of the olefin product mixture. Typically, the first distillation process conditions (for example, T, P) depend upon the specific volatiles and lights to be removed. Typically, the temperature of the first distillation is greater than about 40° C., while the pressure is typically greater than about 15 mm Hg (20 kPa). Typically, the temperature of the first distillation is less than about 150° C., while the pressure is less than about 100 mm Hg (132 kPa). Other process conditions may be suitable, as determined by one skilled in the art.

After removal of lights and volatiles, the metathesis product mixture is fed to a second distillation equipment, preferably, a short-path wiped film evaporator, under conditions sufficient to reduce metal(s) to a concentration of less than about 30 ppm by weight. Short path wiped-film evaporators, known to those of skill in the art, contain internal condensers and a relatively short path from heated surface to condenser surface that renders the pressure drop between the two surfaces negligible. The actual path distance will vary depending upon the scale of the evaporator, for example, from about 1 to about 4 centimeters in a laboratory scale evaporator to about 50 centimeters in a commercial unit. A short path evaporation can be effected at low pressures (typically, from greater than about 0.001 mm Hg (1.3 Pa) to less than about 5 mm Hg (6.6 kPa)), which in turn allow for lower boiling temperatures. Lower boiling temperatures are advantageous, because as noted throughout this description, olefin metathesis product mixtures are more unstable at increasing temperatures due to the presence of metal(s). Additionally, the wiped film evaporator also functions to reduce the thickness of a film and distribute it evenly on the heated surface, which in turn reduces hot spots that could adversely affect thermally unstable compounds.

The temperature and pressure of the short path wiped-film evaporation will also depend upon the specific metathesis products to be distilled. One skilled in the art will know how to vary temperature and pressure of the second distillation to recover the desired products. In a preferred embodiment involving the distillation of 1-decene, methyl decenoate, and methyl oleate, typically, the short path wiped-film evaporation is conducted at a temperature greater than about 150° C. and a pressure greater than about 0.001 mm Hg (1.3 Pa). Typically, in the preferred embodiment the short-path wiped-film evaporation is conducted at a temperature less than about 200° C and a pressure less than about 5 mm Hg (6.6 kPa). The actual pressure used depends upon the requirement to stay below the temperature at which thermal decomposition occurs. Residence time of the metathesis product in the short path wiped-film evaporator is typically in the range of about 15 seconds to about 20 seconds, thereby reducing the heat history on the metathesis product and further minimizing the possibility of thermal degradation. When the distillation is conducted as described hereinabove first to remove volatile and lights and then via a short path wiped-film evaporator, then typically the total concentration of metal(s) in the metathesis product mixture is reduced to less than about 100 ppb, and preferably, less than about 75 ppb by weight.

The following examples are provided as illustrative embodiments of the process and composition of this invention. The examples should not be construed to limit the inventions in any manner. In light of the disclosure herein, those of skill in the art will recognize modifications of the following illustrative embodiments that fall within the scope of the invention.

Preparation of Olefin Metathesis Product Mixture

In a dry box, a solution was prepared of a catalytic ruthenium complex (0.01 M) in toluene, the ruthenium complex being bis(tricyclohexylphosphine)benzylidene ruthenium dichloride (Grubb's catalyst). Methyloleate (Aldrich Company) was degassed with nitrogen and passed through a column of activated alumina prior to use. In a dry box, a reactor was charged with the following reagents: methyloleate (3.50 g, purified as described above), tetradecane (0.50 g, used as an internal standard for gas chromatography analysis), and the catalyst solution (265 microliters, 0.01 M solution). The molar ratio of methyloleate to ruthenium was 4452/1. The reactor was sealed, removed from the dry box, and attached to an ethylene manifold (ethylene, 99.8 percent purity, polymer grade). An olefin metathesis reaction was effected at 60 psig ethylene (413.7 kPa) and 30° C. for 4 hours. Aliquot samples were removed from the reactor and analyzed by gas chromatography. An olefin metathesis product mixture was obtained comprising 1-decene (19.9 area percent) and methyl 9-decenoate (18 area percent), and other components including solvent, methyl oleate and homo-metathesis by-products (62.1 area percent).

EXAMPLES 1-14

The general procedure for stabilizing an olefin metathesis product mixture and removing catalytic metals from said mixture is described as follows. The crude metathesis product mixture obtained hereinabove (10 ml aliquot) containing 65 parts per million ruthenium was stirred with an adsorbent (700 mg) under air for 3 hours at room temperature (22° C.) and ambient pressure. At the end of the contact period, the mixture was filtered through a Teflon™ brand tetrafluoroethylene fluorocarbon polymer filter (0.45 micron diameter) to yield the stabilized olefin metathesis product mixture. The ruthenium content of the stabilized mixture was analyzed by inductively-coupled plasma mass spectrometry (ICP-MS).

The above general procedure was carried out with each of the following adsorbents: Westvaco Nuchar™ SA brand wood carbon (Exp. 1), Westvaco Nuchar™ SA brand carbon that was once used (Exp. 2), Westvaco Nuchar™ SN brand wood carbon (Exp. 3), Westvaco Nuchar™ brand wood carbon modified with copper (Exp. 4), Cabot Monarch™ brand carbon (Exp. 5), Calgon PCB™ coconut carbon (Exp. 6), Westvaco Nuchar™ SA brand wood carbon modified with potassium carbonate and copper (Exp. 7), Black Pearl 2000 brand carbon (Exp. 8), diatomaceous earth (Exp. 9), silica gel (Exp. 10), bentonite clay (Exp. 11), kaolin clay (Exp. 12), Amberlyst™ A21 brand reticulated polystyrene ion-exchange resin (Exp. 13), and montmorillonite clay (Exp. 14). Results are set forth in Table 1.

TABLE 1

Stabilization of Olefin Metathesis Product Mixtures[a,b]

| Experiment | Adsorbent | [Ru] after stabilization (ppb by weight) |
|---|---|---|
| 1 | Wood carbon (Westvaco) | 220 |
| 2 | Wood carbon (Westvaco, used) | 2,000 |
| 3 | Wood carbon (Westvaco) | 170 |
| 4 | Wood carbon (Westvaco, modified) | 850 |
| 5 | Carbon (Cabot) | 14,000 |
| 6 | Coconut carbon (Calgon) | 13,300 |
| 7 | Wood carbon (Westvaco, modified) | 1,140 |
| 8 | Carbon (Black Pearl) | 10,300 |
| 9 | Diatomaceous earth | 13,500 |
| 10 | Silica gel | 3,790 |
| 11 | Clay (Bentonite) | 6,090 |
| 12 | Clay (Kaolin) | 15,100 |
| 13 | Ion-exchange resin (Amberlyst ™) | 1,870 |
| 14 | Clay (Montmorillonite) | 9,520 |

[a]Crude Olefin Metathesis Product Mixture: 1-decene (19.9 area percent), methyl 9-decenoate (18 area percent), balance containing solvent, methyl oleate, and homo-metathesis by-products (62.1 area percent), and 65,000 parts per billion (ppb) ruthenium (65 ppm Ru).
[b]Contacting conditions: 3 h at ambient pressure and temperature (~22° C.); 0.07 g adsorbent per g metathesis product mixture.

From Table 1 it is seen that the adsorbents tested are capable of removing ruthenium to a concentration of less than 30,000 parts per billion (ppb) (30 ppm), by weight, based on the weight of the olefin metathesis product mixture. Unused wood carbon gave the best results, with residual ruthenium concentrations ranging from only 170 ppb to only 1,140 ppb.

EXAMPLES 15-16

Evaluation of Metathesis Reaction Mixture Stability

To determine the stability of an olefin metathesis product mixture to olefin isomerization, two such product mixtures containing methyl 9-decenoate and a ruthenium concentration of 100 ppb (Ex. 15) and 423 ppb (Ex. 16), respectively, were heated to between 200-220° C. and monitored for olefin isomerization by gas phase chromatography analysis. Table 2 illustrates the impact of the heating cycle on the isomerization of methyl 9-decenoate.

TABLE 2

Impact of [Ru] on Olefin Metathesis Product Mixture Stability

| Example | [Ru] (ppb) | Heating Temperature (° C.) | Heating Time (h) | % Isomerized Methyl 9-Decenoate |
|---|---|---|---|---|
| 15[a] | 100 | 210-220 | 2.7 | 0.2 |
| 16[b] | 423 | 200 | 1.0 | 26.3 |
| CE-1[c] | 66,500 | 175 | 1.0 | 27.5 |
|  |  | 175 | 4.0 | 48.1 |

[a]Crude Olefin Metathesis Product Mixture: 1-decene (19.8 area percent), methyl 9-decenoate (19.9 area percent), balance including solvent, methyl oleate, and homo-metathesis by-products (60.3 area percent), and [Ru] as shown.
[b]Crude Olefin Metathesis Product Mixture: 1-decene (19.9 area percent), methyl 9-decenoate (18 area percent), balance including solvent, methyl oleate, and homo-metathesis by-products (62.1 area percent), and [Ru] as shown.
[c]Crude Olefin Metathesis Product Mixture: 1-decene (10.7 area percent), methyl 9-decenoate (14.4 area percent), balance including solvent, methyl oleate, and homo-metathesis by-products (74.9 area percent), and [Ru] as shown.

From Table 2 it is seen that when the ruthenium concentration is lowered from 423 ppb to 100 ppb, a significant increase in stability to isomerization is observed. Specifically, only 0.2% isomerization occurs at 100 ppb ruthenium (Ex. 15), as compared with 26.3% isomerization occurring at 423 ppb ruthenium (Ex. 16), under process conditions wherein the sample of lower ruthenium concentration (Ex. 15) was heated at a slightly higher temperature and for a significantly longer time than the sample of higher ruthenium concentration (Ex. 16). Achieving low ruthenium concentrations is critical in order to prevent olefin isomerization during reaction mixture work-up, purification, and/or isolation. 0

Comparative Experiment 1 (CE-1)

For comparative purposes, an olefin metathesis product mixture was heated at 200-220° C. and monitored for olefin isomerization by gas chromatography analysis in a manner closely similar to that used in Examples 15 and 16, with the exception that the ruthenium concentration in this comparative experiment was 66.5 ppm (66,500 ppb). As shown in Table 2, the comparative product mixture exhibited 27.5 percent isomerization of methyl 9-decenoate at 175° C. over 1 hour and 48.1 percent isomerization of methyl 9-decenoate at 175° C. over 4 hours. The results shown in Table 2 indicate that the comparative olefin metathesis product mixture containing greater than 30 ppm ruthenium exhibited a higher instability to isomerization at lower temperature, as compared with the olefin metathesis product mixtures of Examples 15 and 16 having a ruthenium concentration lower than 30 ppm.

EXAMPLE 17

An olefin metathesis product mixture similar to that used in Example 1 hereinabove, comprising 1-decene, methyl decenoate, homo-metathesis by-products, toluene solvent, and ruthenium metathesis catalyst (65 ppm Ru) was subjected to a first short-path wiped-film evaporation to remove volatiles and lights, including toluene. The evaporator comprised a wiped-film evaporator with internal condenser having a distance from heated surface to cooled surface of 2 centimeters. The evaporator was operated at 115° C. and 30 mm Hg (39 kPa). Bottoms from the first evaporator were fed into a second short-path wiped-film evaporator similar in design to the first evaporator. The second evaporator was operated at higher temperature and lower pressure than the first, namely, 185° C. and 5 mm Hg (6.6 kPa). Residence time of the feed in the second evaporator was estimated to be about 15 to 20 seconds. 1-Decene, methyl decenoate, and roughly one-half of the methyl oleate in the bottoms feed were distilled from the heavies and catalyst. The ruthenium concentration in the overheads from the second distillation stage was reduced to between non-detectable (<50 ppb) and 75 ppb.

What is claimed is:

1. A method of stabilizing an olefin metathesis product mixture comprising subjecting the olefin metathesis product mixture to a first distillation to remove substantially volatiles and lights, and thereafter, subjecting bottoms from the first distillation to a second distillation in a wiped film evaporator; the distillation method being conducted under conditions sufficient to remove metal(s) to a concentration less than about 100 parts per billion by weight.

2. The method of claim 1 wherein the olefin metathesis product mixture comprises a $C_{2-20}$ substituted or unsubstituted olefin or a mixture thereof, and further, wherein the olefin is a monoolefin or a polyolefin.

3. The method of claim 1 wherein the olefin metathesis product mixture comprises a $C_{2-20}$ α-olefin, a $C_{2-20}$ α,ω-unsaturated acid, a $C_{2-20}$ α,ω-unsaturated ester, or a combination thereof.

4. The process of claim 1 wherein the catalytic metal is selected from ruthenium, tungsten, molybdenum, rhenium, or a combination thereof.

5. The process of claim 1 wherein the metathesis catalyst is selected from the group consisting of dichloro-3,3-diphenylvinylcarbene-bis(tricyclohexylphosphine)-ruthenium (II), bis(tricyclohexylphosphine)benzylidene ruthenium dichloride, bis(tricyclohexylphosphine)benzylidene ruthenium dibromide, tricyclohexylphosphine[1,3-bis(2,4,6-trimethylphenyl)-4,5-dihydroimidazol-2-ylidene][benzylidene]ruthenium dichloride, tricyclohexylphosphine[1,3-bis(2,4,6-trimethylphenyl)-4,5-dihydroimidazol-2-ylidene][benzylidene]ruthenium dibromide, and tricyclohexylphosphine[1,3-bis(2,4,6-trimethylphenyl)-4,5-dihydroimidazol-2-ylidene][benzylidene]ruthenium diiodide.

6. The process of claim 1 wherein the metathesis catalyst is selected from dichloro-3,3-diphenylvinylcarbene-bis(tricyclohexylphosphine)-ruthenium (II), bis(tricyclohexylphosphine)benzylidene ruthenium dichloride, tricyclohexylphosphine[1,3-bis(2,4,6-trimethylphenyl)-4,5-dihydroimidazol-2-ylidene]{benzylidene}ruthenium (IV) dichloride, tricyclohexylphosphine[1,3-bis(2,4,6-trimethylphenyl)-4,5-dihydroimidazol-2-ylidene]{benzylidene}ruthenium (IV) dibromide, tricyclohexylphosphine[1,3-bis(2,4,6-trimethylphenyl)-4,5-dihydroimidazol-2-ylidene]{benzylidene}ruthenium (IV) diiodide, and chelated ruthenium complexes represented by the following formula:

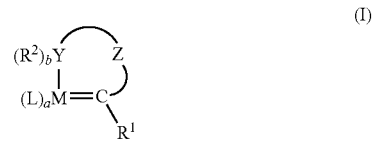

wherein M is Ru; each L is independently selected from neutral and anionic ligands in any combination that balances the bonding and charge requirements of M; a is an integer, preferably from 1 to about 4, which represents the total number of ligands L; $R^1$ is selected from hydrogen, straight-chain or branched alkyl, cycloalkyl, aryl, and substituted aryl radicals; Y is an electron donor group of an element from Group 15 or 16 of the Periodic Table; each $R^2$ is independently selected from hydrogen, alkyl, cycloalkyl, aryl, and substituted aryl radicals sufficient to satisfy the valency of Y; b is an integer, preferably 0 to about 2, representing the total number of $R^2$ radicals; and Z is an organic diradical that is bonded to both Y and the carbene carbon (C) so as to form a bidentate ligand, which ligand in connection with the M atom forms a ring of from about 4 to about 8 atoms.

7. The process of claim 1 wherein the metathesis catalyst is:

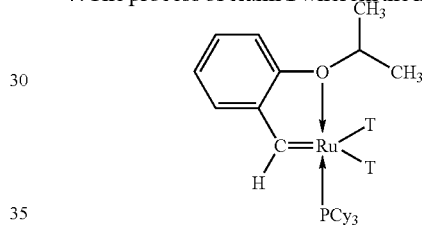

wherein each T is independently selected from Cl and Br, and $PCy_3$ is tricyclohexylphosphine.

8. The process of claim 1 wherein the metathesis catalyst is supported on a catalyst support.

9. The process of claim 1 wherein metals other than those derived from the catalyst and catalyst degradation products are present and the metals are selected from iron, nickel, copper, zinc, cobalt, chromium, lithium, sodium, potassium, magnesium, calcium, and mixtures thereof.

10. The process of claim 1 wherein the catalyst degradation product is derived from the reaction of the ligand with oxygen or water.

11. The process of claim 1 wherein the first distillation to remove lights and volatiles is operated at a temperature greater than about 40° C. and less than about 150° C. and a pressure greater than about 15 mm Hg (20 kPa) and less than about 100 mm Hg (132 kPa).

12. The process of claim 1 wherein the second distillation is conducted in a short path wiped-film evaporator that is operated at a temperature greater than about 150° C. and less than about 200° C. and at a pressure greater than about 0.001 mm Hg (1.3 Pa) and less than about 5 mm Hg (6.6 kPa).

13. The process of claim 1 wherein the concentration of metal(s) after stabilization is less than about 75 parts per billion by weight.

14. The method of claim 1 wherein the olefin metathesis product mixture comprises 1-decene, methyl decenoate, and methyl oleate.

* * * * *

UNITED STATES PATENT AND TRADEMARK OFFICE
CERTIFICATE OF CORRECTION

| | | |
|---|---|---|
| PATENT NO. | : 7,696,398 B2 | Page 1 of 1 |
| APPLICATION NO. | : 10/528472 | |
| DATED | : April 13, 2010 | |
| INVENTOR(S) | : Kenneth A. Burdett, Rob R. Maughon and Patrick H. Au-Yeung | |

It is certified that error appears in the above-identified patent and that said Letters Patent is hereby corrected as shown below:

Title Pg, Item (73) Assignee: should read

-- (73) Assignee: Dow Global Technologies Inc. --

Signed and Sealed this
Fifth Day of April, 2011

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,696,398 B2 |
| APPLICATION NO. | : 10/528472 |
| DATED | : April 13, 2010 |
| INVENTOR(S) | : Kenneth A. Burdett et al. |

It is certified that error appears in the above-identified patent and that said Letters Patent is hereby corrected as shown below:

In the specification, page one is amended by adding a paragraph before the Cross-Reference to Related Applications paragraph on page 1, line 2 to read as follows:

This invention was made with U.S. Government support under contract DE-FC36-01ID14213 awarded by the Department of Energy. The U.S. Government has certain rights in this invention.

Signed and Sealed this
Twenty-seventh Day of November, 2012

David J. Kappos
*Director of the United States Patent and Trademark Office*